United States Patent [19]

Westermann et al.

[11] Patent Number: 5,523,428
[45] Date of Patent: Jun. 4, 1996

[54] PROCESS FOR THE PRODUCTION OF 1-METHYL-3-KETO-$\Delta^{1,4}$ STEROIDS

[75] Inventors: Jürgen Westermann; Klaus Nickisch; Annette Prelle, all of Berlin, Germany

[73] Assignee: Schering Aktiengesellschaft, Berlin, Germany

[21] Appl. No.: 381,980

[22] PCT Filed: Jun. 22, 1993

[86] PCT No.: PCT/EP93/01606

§ 371 Date: Apr. 18, 1995

§ 102(e) Date: Apr. 18, 1995

[87] PCT Pub. No.: WO94/04553

PCT Pub. Date: Mar. 3, 1994

[30] Foreign Application Priority Data

Aug. 13, 1992 [DE] Germany .................. 42 27 053.7

[51] Int. Cl.$^6$ ............................................. C07J 1/00
[52] U.S. Cl. ................... 552/634; 540/31; 552/603; 552/611; 552/544; 552/552; 552/555
[58] Field of Search ........................ 540/31; 552/544, 552/552, 555, 603, 611, 634

[56] References Cited

U.S. PATENT DOCUMENTS

| | | | |
|---|---|---|---|
| 4,022,769 | 5/1977 | Grunwell et al. | 424/241 |
| 4,071,624 | 1/1978 | Grunwell et al. | 424/238 |
| 4,071,625 | 1/1978 | Grunwell et al. | 424/238 |

FOREIGN PATENT DOCUMENTS

| | | |
|---|---|---|
| 0290378 | 11/1988 | European Pat. Off. . |
| 0534582A1 | 3/1993 | European Pat. Off. . |

OTHER PUBLICATIONS

PCT Search Report dated Oct. 25, 1993.
Australian Journal of Chemistry, *"Nickel–Catalysed Conjugate Addition of Trimethylaluminum to α,β–Unsaturated Ketones"*, vol. 28, Melbourne 1975.
Australian Journal of Chemistry, *"Nickel–Catalysed Conjugate Addition of Trimethylaluminum to 3–Oxo–$\Delta^4$–Steroids"*, vol. 28, Melbourne 1975.

Journal of Organic Chemistry, *"Transition Metal Catalyzed Conjugate Methylation of α,β–Unsaturated Ketones by Trimethylaluminum and Lithium Tetramethylaluminate"*, vol. 39, No. 22, Nov. 1974.

Primary Examiner—Kimberly J. Prior
Attorney, Agent, or Firm—Millen, White, Zelano, & Branigan

[57] ABSTRACT

A process for the production of 1-methyl-3-keto-$\Delta^{1,4}$ steroids of general formula I

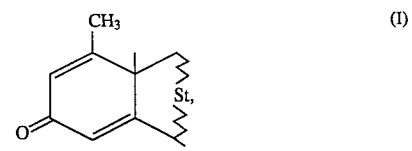

in which St symbolizes the radical of asteroid molecule, where a 3-keto-$\Delta^{1,4}$ steroid of general formula II

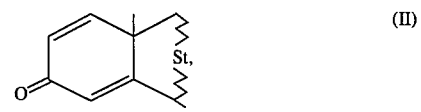

in which St has the above-mentioned meaning, is reacted in an inert solvent in the presence of a nickel salt soluble therein with an organometallic compound of formula III, IV or V

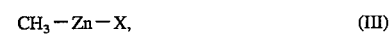

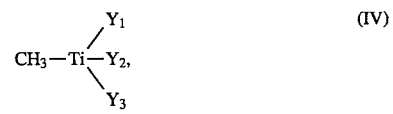

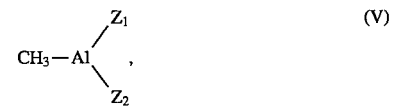

where X, $Y_1$, $Y_2$, $Y_3$, $Z_1$ and $Z_2$ are as defined in the specification.

5 Claims, No Drawings

PROCESS FOR THE PRODUCTION OF 1-METHYL-3-KETO-Δ$^{1,4}$ STEROIDS

This application is a 371 of PCT/EP93/01606 filed Jun. 22, 1993.

The invention relates to a process for the production of 1-methyl- 3-keto-Δ$^{1,4}$ steroids of general formula I

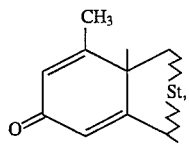     (I)

in which

St symbolizes the radical of asteroid molecule, characterized in that a 3-keto-Δ$^{1,4}$ steroid of general formula II

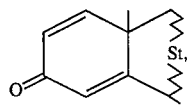     (II)

in which

St has the above-mentioned meaning, is reacted in an inert solvent in the presence of a nickel salt soluble herein with an organometallic compound of formula III, IV or V

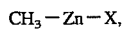     (III)

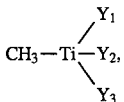     (IV)

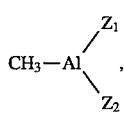     (V)

in which

X represents a methyl group, an alkoxy group with at most 6 carbon atoms or a phenoxy radical optionally substituted by halogen atoms, alkoxy groups with at most 6 carbon atoms and/or alkyl groups with at most 6 carbon atoms, and $Y_1$, $Y_2$ and $Y_3$ as well as $Z_1$ and $Z_2$ are the same or different and have the same meaning as X.

The invention preferably relates to a process for the production of 1-methyl-3-keto-Δ$^{1,4}$ steroids of general formula Ia

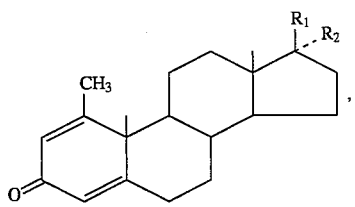     (Ia)

in which $R_1$ and $R_2$ together represent an oxo group or an alkylenedioxy group with 2 to 6 carbon atoms or in which $R_1$ means an acyloxy group with up to 8 carbon atoms or an alkyl radical with at most 10 carbon atoms and $R_2$ symbolizes a hydrogen atom under the above-mentioned conditions from 3-keto-Δ$^{1,4}$ steroids of general formula IIa

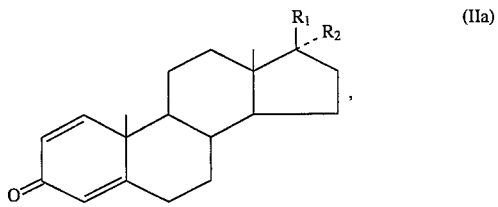     (IIa)

in which $R_1$ and $R_2$ have the above-mentioned meaning.

An alkylenedioxy group $R_1$ and $R_2$ preferably is to be understood to be, for example, an ethylenedioxy group, a 1,3-propylenedioxy group, a 2,2-dimethylpropylenedioxy group or a 2,3-butylenedioxy group.

An acyloxy group $R_1$ of the compounds preferably is to be understood to be an alkanoyl group, such as the acetoxy group, the propionyloxy group, the butyryloxy group, the trimethylacetoxy group, etc. or the benzoyloxy group.

An alkyl radical $R_1$ preferably is to be understood to be one with 8 to 10 carbon atoms, as it is present in the side chains of naturally occurring zoosterols or phytosterols, such as cholesterol, campesterol or β-sitosterol.

It is known that the 1-methyl-androsta-1,4-diene-3,17-dione (=atamestane) is a pharmacologically effective compound, but whose multistage synthesis of androsta-1,4-diene-3,17-dione is quite expensive (DE-A 40 15 247). In contrast, the process according to the invention makes it possible to perform this reaction in one reaction step. That this is possible is surprising to one skilled in the art, since it is known that under comparable conditions, 3-keto-Δ$^4$ steroids are methylated in 5β-position (Aust. J. Chem. 1975, 28, 817ff). Also, the other compounds of general formula Ia can be converted in a simple way to atamestane, by the 17-esters or 17-ketals being saponified and then the 17-hydroxy group being oxidized in a known way (DE-A 33 22 285) or by the side chain of the sterol derivatives of general formula Ia being microbiologically degraded under conditions as they are described in U.S. Pat. No. 4,100,026.

The process according to the invention is performed in an inert solvent. Suitable solvents are aliphatic, cycloaliphatic, or aromatic liquid hydrocarbons, such as hexane, petroleum ether, cyclohexane, benzene, toluene or xylene, ethers, such as diethyl ether, diisopropyl ether, tetrahydrofuran or dioxane, esters, such as ethyl acetate, methyl acetate or mixtures of these solvents.

The reaction is performed in the presence of nickel salts, which are soluble in these solvents or solvent mixtures. Suitable nickel salts are, for example, the nickel(II)-bis-(triphenylphosphine)-chloride, the tetrakis-(triphenylphosphine)nickel(O), the nickel(II)-stearate, the bis-diethyloxalacetatol)-nickel, the pentakis-(ethylacetatolhydroxotrinickel, the bis(1,3-diphenylpropane-1,3-dionatolnickel, the bis(acrolein)-nickel(O) and especially the nickel(II)-acetylacetonate (Aust. J. Chem., 1974, 27, 2569 ff and Aust. J. Chem., 1975, 28, 801 ff). For reaction, preferably 0.01–0.1 mol of nickel salt per mol of steroid to be reacted is used. According to the invention, an organometallic compound of formula III, IV or V is used to methylate the steroid. As a suitable organometallic compound of general formula II, for example, the dimethyl zinc can be mentioned. An organometallic compound of formula IV is, for example, the methyl-triisopropyloxy-titanium (J. Organomet. Chem., 1974, 74, 85 ff). The methylation preferably takes place with aluminum-organic compounds of general formula V, in which relative to the trimethylaluminum, those compounds are especially preferred in which one or both radicals $Z_1$ and $Z_2$ represent an alkoxy group or an optionally substituted phenoxyradical.

These compounds can be produced in a simple way, by, for example, a solution of trimethylaluminum being reacted in a hydrocarbon radical with the stoichiometrically required amount of an alcohol or a preferably sterically hindered phenol. (T. Mole and E. Jeffry in "Organoaluminum Compounds," Elviser Publishing Comp., Amsterdam, London, New York 1972 and J. Org. Chem. 1979, 26, 4792 ff).

Suitable alcohols are, for example, methanol, ethanol, isopropanol or tert-butanol; as suitable phenols, there can be mentioned, for example, the 2,6-di-tert-butylphenol, 2-tert-butyl- 6-methylphenol, 2,4,6-tri-tert-butylphenol, 2,6-di-tert-butyl- 4-bromophenol or especially also the 2,6-di-tert-butyl-4-methylphenol.

To perform the reaction, preferably 0.3 to 1.2 mol, 1 to 1.5 times the theoretically required amount of organometallic compound is used.

The reaction itself can be performed, for example, so that a solution of the steroid to be reacted is put into a solution of the organometallic compound, the nickel catalyst is added and the mixture is heated to 40° C. to 80° C. But, on the other hand, the nickel catalyst can also be introduced with the steroid and the organometallic compound can be added.

After completion of the reaction, which can be determined, for example, by thin-layer chromatographical or gas chromatographical analysis, the reaction mixture is worked-up in a way known in the art, and the reaction product is purified by chromatography and/or recrystallization.

The following embodiments are used for a more detailed explanation of the process according to the invention.

EXAMPLE 1

1-Methyl-androsta-1,4-diene-3,17-dione 12 ml (12 mmol) of trimethylaluminum of a 10% solution in hexane is introduced at room temperature under nitrogen atmosphere. With stirring, 2.64 g of 2,6-di-tert-butyl-4-methylphenol is added in portions. The solution is stirred for 30 more minutes and 2.84 g (10 mmol) of androsta-1,4-diene-3,17-dione in 20 ml of ethyl acetate is added at 25° C. The solution is heated to 58° C. At 58° C., 143 mg of nickel(II)-acetylacetonate is added. The solution is stirred for 2.5 more hours at a temperature of 60° C. After cooling, 1.1 ml of water is added for hydrolysis and stirred for 15 minutes. The inorganic solid is filtered off and rewashed twice with 50 ml of ethyl acetate. After concentration by evaporation of the ethyl acetate phases, a crude product is obtained, which is chromatographed on silica gel with hexane/ethyl acetate as eluent with increasing ethyl acetate portion. 1.5 g of initial material is recovered. 0.60 g of 1-methyl-androsta- 1,4-diene-3,17-dione of melting point 168°–170° C. is obtained. The yield is 20% of theory or 42% taking into consideration the initial material recovered.

EXAMPLE 2

17β-Acetoxy-1-methyl-androsta-1,4-dien-3-one 12 ml of trimethylaluminum of a 10% solution in hexane (12 mmol) is introduced at room temperature under nitrogen atmosphere. With stirring, 2.64 g of 2,6-di-tert-butyl-4-methylphenol is added in portions. The solution is stirred for 30 more minutes and 3.27 g (10 mmol) of 17β-acetoxy-androsta-1,4-dien- 3-one in 20 ml of ethyl acetate is added at 25° C. The solution is heated to 60° C. and 143 mg of nickel(II)-acetylacetonate is added at 60° C. The solution is stirred for another 2.5 hours at this temperature. After cooling, 1.1 ml water is added for hydrolysis and stirred for 15 minutes. The solid is filtered off, rewashed twice-with 50 ml of ethyl, acetate. After concentration by evaporation of the ethyl acetate phases, a crude product is obtained, which is chromatographed on silica gel with hexane/ethyl acetate as eluent with increasing ethyl acetate portion. 1.55 g of initial material is recovered. 0.68 g of 17β-acetoxy-1-methyl-androsta-1,4-dien-3-one of melting point 144.1° C. is obtained. The yield is 20% of theory or 38% taking into consideration the initial material recovered.

EXAMPLE 3

1-Methyl-androsta-1,4-diene-3,17-dione 86.4 ml (80 mmol) of a 10% solution of trimethylaluminum in hexane is introduced at room temperature under nitrogen atmosphere. With stirring, 17.4 g (80 mmol) of 2,6-di-tert-butyl- 4-methylphenol is added in portions. The solution is stirred for 30 more minutes and subsequently stirred until the end of the methane generation. 28.4 g (100 mmol) of androsta- 1,4-diene-3,17-dione (ADD) in 200 ml of methyl acetate is added at 25° C. The solution is heated to 50° C. 1.43 g (5 mmol) of nickel(II)-acetylacetonate is added at 50° C. The solution is stirred for 50 more minutes at a temperature of 50° C. For hydrolysis, 15 ml of water is added with cooling, for completion, it is stirred for 15 more minutes. The inorganic solid is filtered off and rewashed twice with 50 ml of methyl acetate. After concentration by evaporation Of the methyl acetate phases, 43.71 g of crude product is obtained, which is chromatographed on silica gel with hexane/ethyl acetate as eluent with increasing ethyl acetate portion. After concentration by evaporation of the fractions, 6.5 g of 1-methyl-androsta-1,4-diene-3,17-dione (23% of theory) of melting point 168° C. is obtained.

EXAMPLE 4 a)
1-Methyl-androsta-1,4-diene-3,17-dione-17-ethylene ketal 32.22 (mmol) of a 10% solution of trimethylaluminum in hexane is introduced at room temperature under nitrogen atmosphere. With stirring, 6.6 g (30 mmol)-of 2,6-di-tert-butyl- 4-methylphenol is added in portions. The solution is stirred for 30 more minutes at 35° C. This thus produced solution of dimethylaluminum-2,6-di-tert-butyl-4-methylphenoxide is added at 58° C. to a solution of 9.84 g (30 mmol) of androsta-1,4-diene- 3,17-dione (ADD) and 430 mg (1.5 mmol) of nickel(II)-acetylacetonate in 60 ml of ethyl acetate (acetic acid-ethyl ester). The solution is stirred for 4 more hours at a temperature of 60° C. For hydrolysis, 5 ml of water is added with cooling. The inorganic solid is filtered off and rewashed twice with 20 ml of ethyl acetate. After concentration by evaporation of the ethyl acetate phases, 17 g of crude,material is obtained, which is chromatographed on silica gel with hexane/ethyl acetate as eluent with increasing ethyl acetate portion. After concentration by evaporation of the fractions, 12.9 g of 1-methyl-androsta- 1,4-diene-3,17-dione-17-ethylene ketal (28% of theory) of melting point 159° C. is obtained.

b) 1-Methyl-androsta-1,4-diene-3,17-dione 3.42 g (10 mmol) of 1-methyl-androsta-1,4-diene-3,17-dione- 17-ethylene-ketal of example 4a is dissolved in 20 ml of ethanol. 3 ml of 2 n sulfuric acid is added and the solution is stirred for 4 hours at room temperature. The reaction mixture is added to 60 ml of ice water and filtered. Crystallization of the precipitate from 10 ml of ethyl acetate yields 2.65 g of 1-methyl-androsta- 1,4-diene-3,17-dione (88% of theory) of melting point 170° C.

We claim:

1. A process for the production of 1-methyl-3-keto-$\Delta^{1,4}$ steroids of general formula I

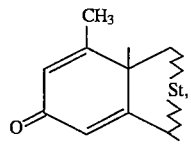
(I)

in which

St symbolizes the radical of asteroid molecule, comprising reacting a 3-keto-$\Delta^{1,4}$ steroid of general formula II

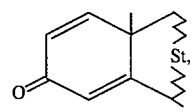
(II)

in which

St has the above-mentioned meaning, in an inert solvent in the presence of a nickel salt soluble therein with an organometallic compound of formula III, IV or V

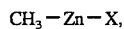
(III)

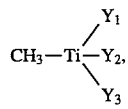
(IV)

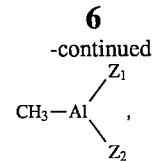
(V)

in which

X represents a methyl group, an alkoxy group with at most 6 carbon atoms or a phenoxy radical optionally substituted by halogen atoms, alkoxy groups with at most 6 carbon atoms and/or alkyl groups with at most 6 carbon atoms, and $Y_1$, $Y_2$ and $Y_3$ as well as $Z_1$ and $Z_2$ are the same or different and have the same meaning as X.

2. The process according to claim 1 wherein the compound of formula II is reacted with an organometallic compound of formula III as defined in claim 1.

3. The process according to claim 1 wherein the compound of formula II is reacted with an organometallic compound of formula IV as defined in claim 1.

4. The process according to claim 1 wherein the compound of formula II is reacted with an organometallic compound of formula V as defined in claim 1.

5. The process according to claim 1 in which the 1-methyl-3-keto-$\Delta^{1,4}$ steroid produced is atamestane.

* * * * *